United States Patent [19]
Tower

[11] Patent Number: 5,860,966
[45] Date of Patent: Jan. 19, 1999

[54] METHOD OF SECURING A STENT ON A BALLOON CATHETER

[75] Inventor: Allen J. Tower, North Lawrence, N.Y.

[73] Assignee: NuMed, Inc., Nicholville, N.Y.

[21] Appl. No.: 834,430

[22] Filed: Apr. 16, 1997

[51] Int. Cl.⁶ .................................................. A61B 17/00
[52] U.S. Cl. ................................................ 606/1; 606/198
[58] Field of Search ...................... 606/1, 108, 191–200; 623/1, 11, 12

[56] References Cited

U.S. PATENT DOCUMENTS

| | | |
|---|---|---|
| 4,733,665 | 3/1988 | Palmaz . |
| 5,161,547 | 11/1992 | Tower . |
| 5,217,483 | 6/1993 | Tower . |
| 5,352,199 | 10/1994 | Tower . |
| 5,389,106 | 2/1995 | Tower . |
| 5,613,981 | 3/1997 | Boyle et al. . |
| 5,628,754 | 5/1997 | Shevlin et al. .......................... 606/108 |

*Primary Examiner*—Glenn K. Dawson
*Attorney, Agent, or Firm*—Wall Marjama Bilinski & Burr

[57] ABSTRACT

Apparatus for securing a stent upon a balloon catheter. The apparatus has a tubular housing that is open at each end for containing a balloon catheter in a deflated state upon which is mounted a stent. An inflatable cylindrical membrane is mounted inside the housing and sealed at both ends to provide a fluid tight chamber between the membrane and the housing. A pressurized fluid is introduced into the chamber to inflate the membrane into pressure contact with the stent to urge the stent into gripping engagement with the balloon.

13 Claims, 3 Drawing Sheets

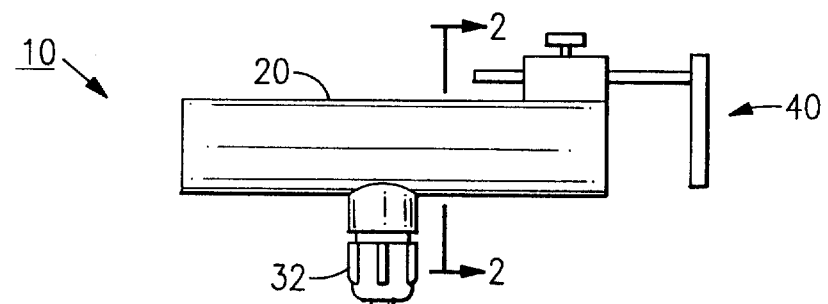
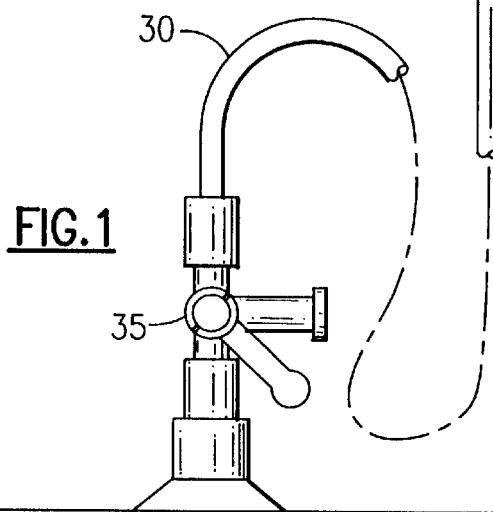
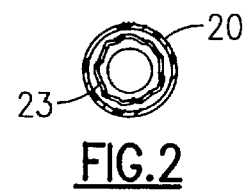
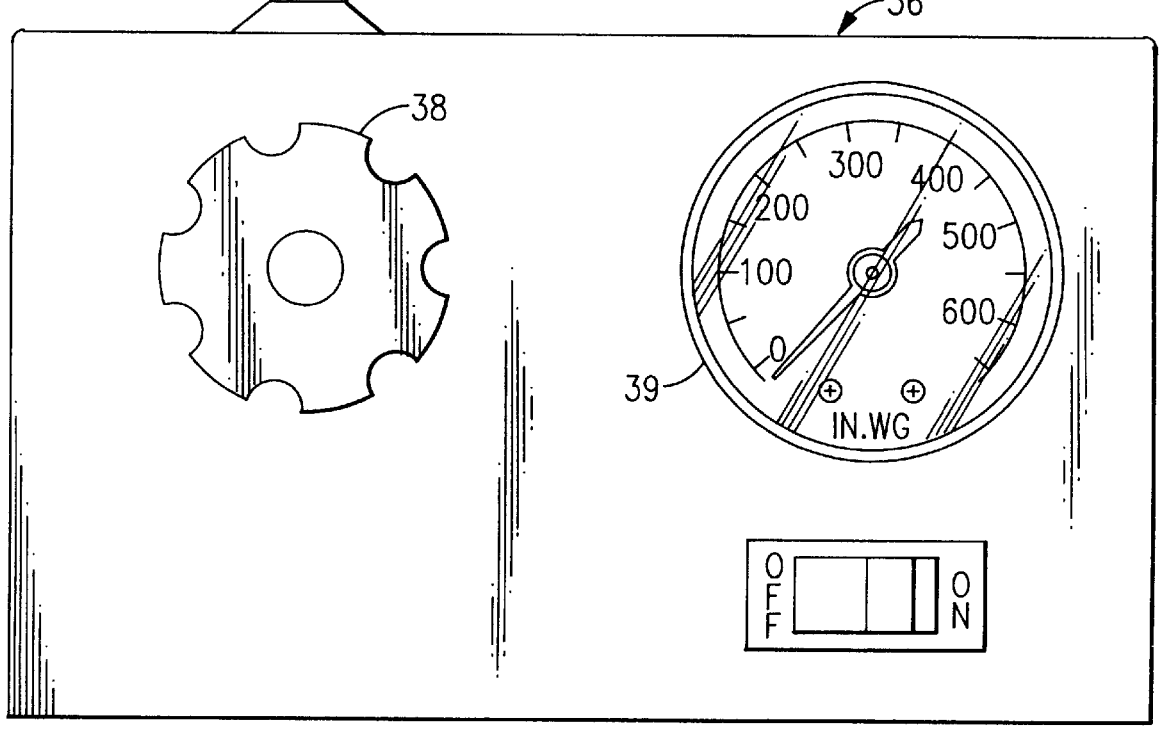
FIG. 1
FIG. 2

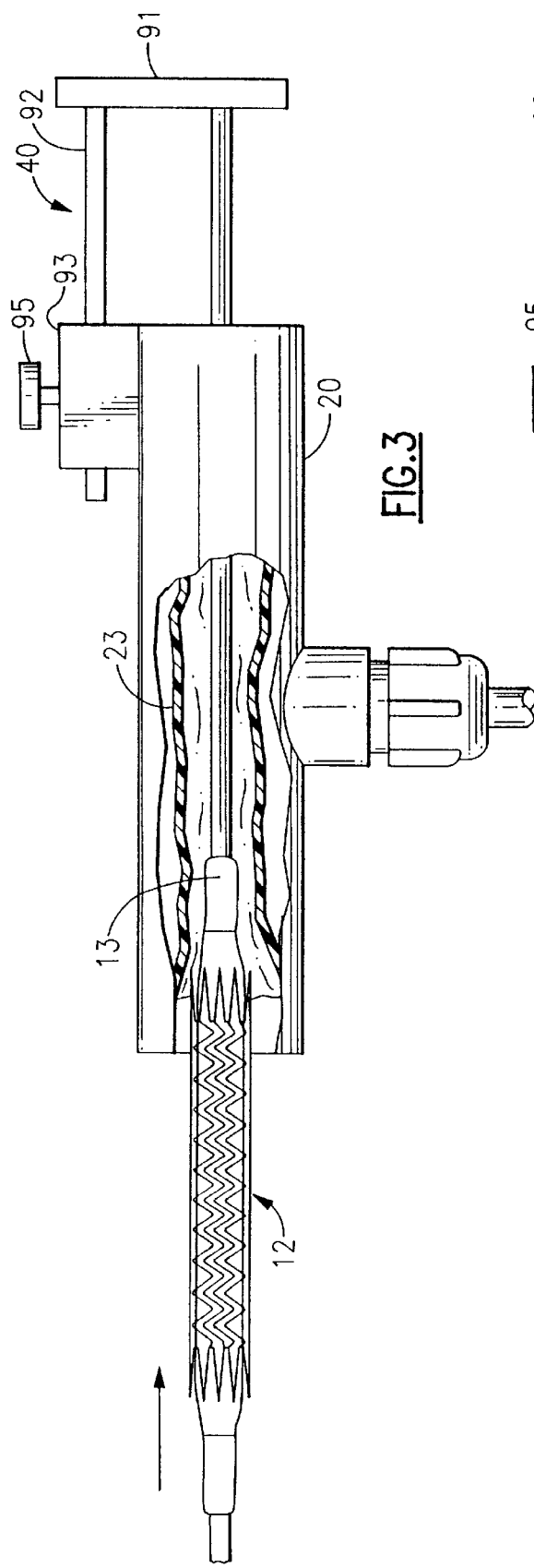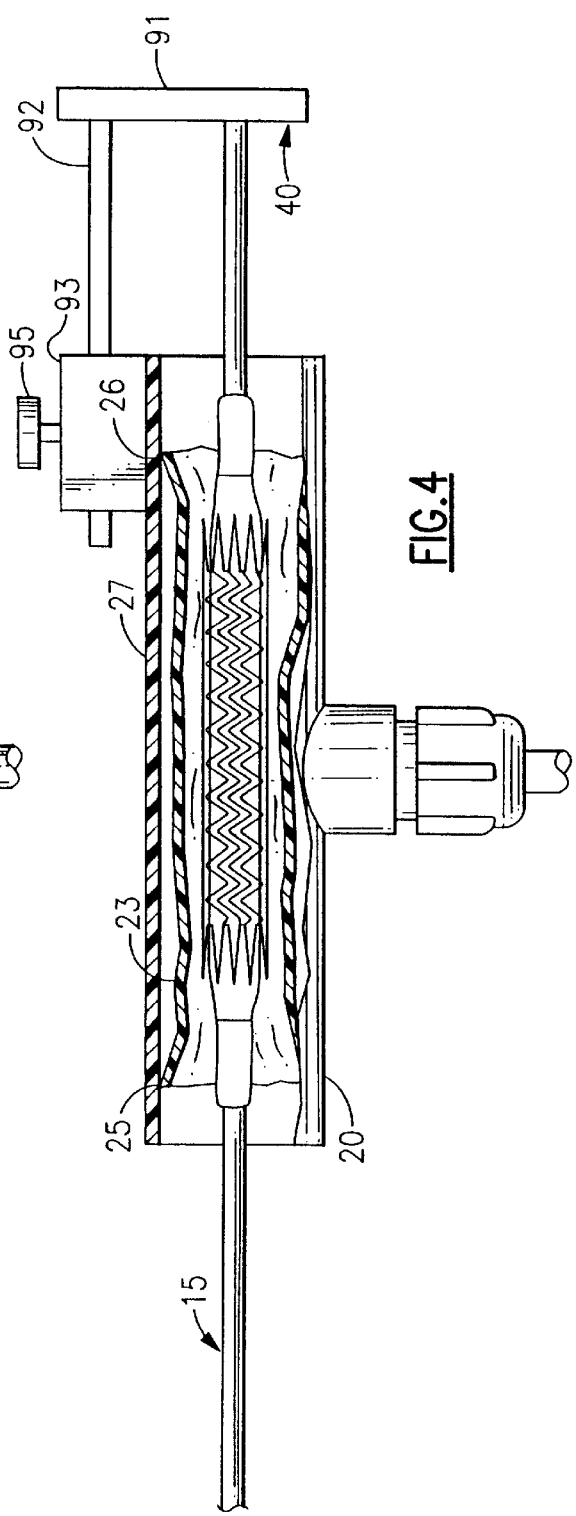

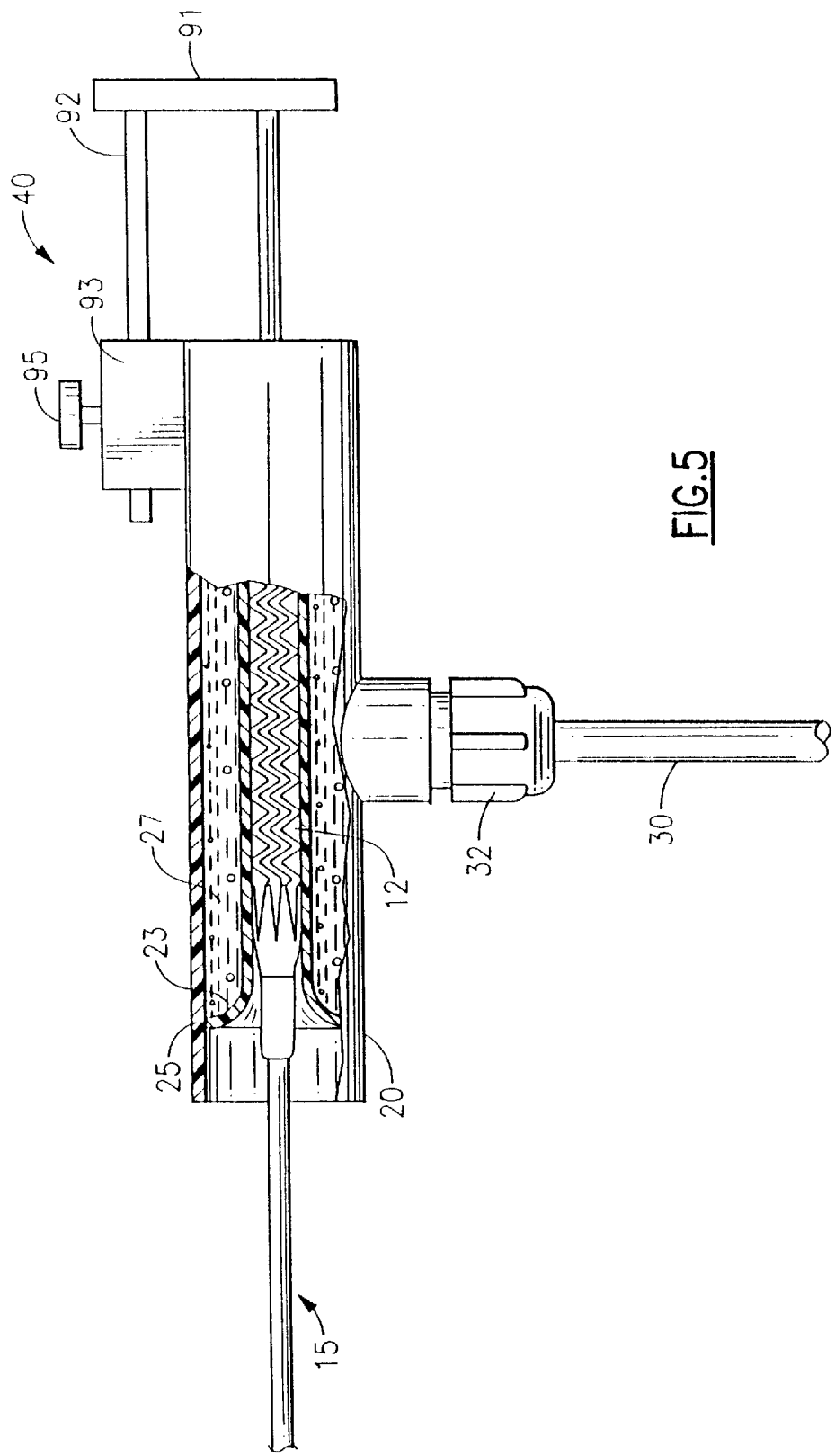

ically, the stent is mounted over a balloon at the distal end of the catheter and is carried into a treatment zone through a blood vessel. Once properly positioned in the treatment zone, the balloon is inflated to expand the stent

METHOD OF SECURING A STENT ON A BALLOON CATHETER

BACKGROUND OF THE INVENTION

This invention relates to stents, and in particular, to a method and apparatus for securely mounting a stent on a balloon catheter.

It is well known that a balloon catheter is well suited for use as a delivery and implantation system for an expandable stent. Typically, the stent is mounted over a balloon at the distal end of the catheter and is carried into a treatment zone through a blood vessel. Once properly positioned in the treatment zone, the balloon is inflated to expand the stent radially to open an occlude passage in the vessel caused by plaque or an aneurism. The catheter, during insertion, must oftentimes travel a rather tortuous path before reaching the treatment zone. If the stent is not securely mounted upon the balloon it can become dislodged or misaligned thus rendering the procedure ineffective. In severe cases, the stent may become entirely dislodged from the catheter while it is inside the patient, thus requiring its recovery through surgical procedures.

In an effort to more securely mount a stent upon a balloon catheter, it is common practice to compress the stent inwardly using special crimping tools similar to pliers. Because the crimping forces are applied repeatedly in different localized regions about the stent, the holding force around the stent tends to be non-uniform which can adversely effect the way the stent expands as the balloon inflates, thus leading to less than satisfactory implantation. More importantly, because the amount of force applied during the crimping operation is generally unregulated, the stent can penetrate the balloon rendering it uninflatable. The fact the balloon has been punctured by the stent generally is not discovered until such time as the stent has been positioned in the body. As a result, the catheter and stent must be retrieved from inside the patient and the procedure repeated.

Cylindrical crimping devices have also been devised wherein the balloon with a stent mounted thereupon are drawn into a cylinder having a predetermined inside diameter. The inside diameter of the cylinder is selected so that ideally the stent is collapsed just enough to apply a non-damaging, yet secure gripping force upon the balloon. This ideal relationship unfortunately is difficult to achieve in practice and puncturing of the balloon by the stent is not uncommon. Accurately guiding the stent bearing balloon into the cylinder can also be difficult and the stent may become misaligned or dislodged during this procedure.

SUMMARY OF THE INVENTION

It is therefore an object of this invention to securely mount an expandable stent upon a balloon catheter without harming the balloon.

A further object of the present invention is to improve the safety of stent delivery systems using balloon catheters.

A still further object of the present invention is to apply a uniform collapsing pressure to a stent as it is being mounted upon a deflated balloon at the distal end of a catheter.

Another object of the present invention is to protect the integrity of a balloon as an unexpanded stent is being secured thereto.

Yet another object of the present invention is to improve the reliability of balloon catheter delivery systems.

These and other objects of the present invention are attained by a tubular housing that is open at each end for containing a balloon catheter in a deflated condition upon which is mounted a stent. An inflatable cylindrical membrane is mounted in the opening of the housing and is sealed against the housing to establish a leak-tight chamber therebetween. A pressurized fluid is introduced into the chamber to expand the membrane into contact with the stent to apply a uniform pressure thereagainst to urge the stent into secure gripping contact with the balloon.

BRIEF DESCRIPTION OF THE DRAWINGS

For a better understanding of these and other objects of the present invention, reference will be made to the detailed description below which is to be read in association with the following drawings, wherein:

FIG. 1 is a side elevation of apparatus embodying the teachings of the present invention;

FIG. 2 is a sectional view taken along lines 2—2 in FIG. 1;

FIG. 3 is an enlarged side elevation with portions broken away showing a balloon catheter carrying a stent being inserted into the housing of the present apparatus;

FIG. 4 is a side elevation similar to that illustrated in FIG. 3 showing the stent and the balloon of the catheter centered in the housing; and FIG. 5 is also a side elevation showing the stent being compressed into gripping contact against the balloon.

DESCRIPTION OF THE INVENTION

Turning now to the drawings, there is shown stent mounting apparatus, generally referenced 10, for securing an expandable stent 12 upon a balloon 13 located at the distal end of a catheter 15. As is well known, the elongated body of the catheter contains at least one lumen that is adapted to carry air or fluid under pressure to the balloon whereby the balloon can be inflated to expand an occluded blood vessel or the like. The balloon catheter can also serve as a delivery vehicle for an expandable stent which is mounted upon the balloon and is guided into an occluded area caused by plaque, an aneurism or the like. Once the stent is properly inserted and its position verified by fluoroscopic means, the balloon is inflated to expand the stent into contact with the occluded vessel, thus opening the vessel. The stent remains in the expanded condition when the balloon is deflated, thus supporting the vessel in the expanded state.

As disclosed in U.S. Pat. No. 5,217,483, the present stent can be formed of a fully annealed platinum wire that is shaped into a cylinder that can be easily slipped over the deflated balloon of a catheter. As the stent is guided by the catheter through a blood vessel, it generally must move through a rather tortuous path of travel. Unless the stent is firmly attached to the balloon, it can become misaligned whereby it will not inflate properly or it may become dislodged entirely from the balloon which, in severe cases, may require a surgical recovery. As noted above, the stent is typically crimped against the balloon to force the stent into gripping contact with the balloon. The prior art method of attaching a stent to a balloon generally involved the application of uncontrolled, non-uniform compression forces to the stent which can result in the balloon becoming punctured when too much force is applied or the stent becoming misaligned during insertion when too little force is applied.

The apparatus of the present invention is specifically designed to apply a controlled, uniformly distributed crimping force to the stent which will provide the maximum desired gripping pressure to the balloon without causing damage to the balloon.

The apparatus of the present invention includes a tubular housing 20 having an axially disposed cylindrical opening passing therethrough. The housing is open at both ends to permit the distal end of a balloon catheter 15 to pass therethrough. A stent 12 is loosely inserted over the deflated balloon 13 in a non-expanded condition. An inflatable cylindrical shaped membrane 23 is contained within the housing opening and both ends of the membrane are joined to the housing using a suitable epoxy or the like to form end seals 25 and 26, thus creating a fluid-tight chamber 27 between the inner wall of the housing and the membrane. The membrane can be fabricated from any suitable material, however, nylon is preferred.

The chamber 27 is placed in communication with an air line 30 (FIG. 1) by means of a threaded connection 32. The other end of the air line is, in turn, connected to a three-way valve 35 mounted upon an air compressor unit 36. Although not shown, the unit contains a small electrically driven compressor, the discharge side of which is connected to the valve 35. A pressure control valve (not shown) is mounted in the unit to regulate the output of the compressor. The desired pressure is set by a control knob 38 and registered by a gauge 39. Alternately, a compressed air source (not shown) or an indeflator (not shown) can be used to supply air or fluid under pressure to the membrane.

As illustrated in FIG. 3, the chamber 27 is initially deflated by opening valve 35 to atmosphere and the distal end of the balloon catheter is passed axially into the housing. An adjustable stop generally referenced 40 is mounted on the housing that is arranged to intercept the end of the catheter when the stent is centered inside the membrane. The axial length of the membrane is greater than the axial length of the stent, the reason for which will become apparent from the description below. Alternately, the housing and the membrane can be made from transparent materials to allow a user to visually position the catheter therein.

Once the stent is centered in the membrane, as shown in FIG. 4, the valve 35 is closed to atmosphere and the compressor brought up to a desired operating pressure. Valve 35 is now cycled to allow compressed air under a desired pressure to enter the chamber 27 thus inflating the membrane.

As illustrated in FIG. 5, the inflated membrane expands inwardly to completely embrace the stent about its entire outer surface area. Accordingly, the stent is urged inwardly at a controlled pressure to firmly grip the balloon. A pressure of at least, 300 psi, according to the present embodiment, is suitable for deforming the membrane. Because of the ability of the stent to hold the position in which it is placed, it will remain in gripping contact when the membrane is deflated. The membrane is then deflated as described and the catheter removed from the housing.

The housing is provided with the above mentioned stop 40 that can be adjusted to help center the stent inside the inflatable membrane. The stop includes a stop plate 91 that is suspended at the distal end of a rod 92. The rod, in turn, is slidably retained within a block 93 mounted on top of the housing. The stop plate is arranged to depend downwardly from the rod past the axial center line of the housing so that it can intercept the distal end of the catheter and thus interrupt its forward progress as it is passed through the housing. The position of the stop plate is set so that when the catheter is intercepted by the plate, the stent and the balloon upon which it is mounted are about centered within the membrane. Accordingly, when the membrane is inflated, it will completely envelope the stent and urge it inwardly under a controlled pressure to uniformly embrace the balloon. Once brought to a desired position, the plate is optionally locked in place using a threaded set screw 95. In a separate embodiment, not shown, a spiral wound sleeve can be used in lieu of the housing and membrane which can be disposed or wound in overlaying relationship to the stent as placed on the collapsed catheter balloon. The sleeve is fixed at one end and can be pulled at its remaining end under a controlled pressure to uniformly apply force to the outer surface of the stent thereby compressing the stent radially to the catheter balloon.

While this invention has been explained with reference to the structure disclosed herein, it is not confined to the details set forth and this invention is intended to cover any modifications and changes as may come within the scope of the following claims:

What is claimed is:

1. Apparatus for securing a stent upon a balloon catheter that includes:

a tubular housing that is open at each end and sized for receiving a balloon catheter having a stent mounted upon a balloon, an inflatable membrane mounted in axial alignment between the ends of said housing, sealing means for sealing respective ends of said membrane to the housing to provide a fluid tight chamber between the membrane and said housing, inflation means for introducing a fluid under pressure into said chamber to inflate said membrane into pressure contact with said stent to uniformly urge the stent into clamping engagement with said balloon, and positioning means for aligning the stent within the housing.

2. The apparatus of claim 1 wherein the membrane is formed of a deformable material capable of being expanded to at least 300 psi.

3. The apparatus of claim 2, wherein the membrane is formed of nylon.

4. The apparatus of claim 1 wherein the axial length of the membrane is sized to be greater than that of the balloon whereby the membrane completely envelopes the balloon when the membrane is inflated.

5. The apparatus of claim 1, that further includes pressure regulator means for controlling the pressure of the fluid introduced into the chamber.

6. The apparatus of claim 5 that further includes a relief valve for releasing pressurized fluid from said chamber.

7. The apparatus of claim 1 wherein the chamber is inflated with compressed air.

8. The apparatus of claim 1, wherein the positioning means is adjustable.

9. The aparatus of claim 1 wherein the housing and the membrane are formed of a transparent material.

10. A method of securing an expandable stent upon a balloon mounted upon a catheter that includes the steps of:

providing an elongated tubular housing having an opening passing therethrough, mounting a cylindrical inflatable membrane within the housing opening, inserting a balloon catheter carrying a stent upon the balloon into the housing opening and axially centering the stent within the membrane, positioning the stent relative to the membrane within the housing, and introducing a fluid under pressure into the membrane to expand the membrane into pressure contact with said stent to urge the stent into gripping contact with the balloon.

11. The method of claim 10 that includes the further step of controlling the pressure of fluid introduced into the membrane.

12. The method of claim 10 that includes a further step of releasing the fluid from said membrane after the stent has been urged into contact with the balloon membrane.

13. The method of claim 10 that includes the further step of sealing both ends of the membrane to the housing to provide a fluid-tight chamber between the inside wall of the housing and the membrane.

* * * * *